(12) United States Patent
Lemmens et al.

(10) Patent No.: US 6,916,919 B2
(45) Date of Patent: Jul. 12, 2005

(54) ISOLATION OF DNA MOLECULES

(75) Inventors: Raf Lemmens, Uppsala (SE); Tomas Nyhammar, Uppsala (SE); Jan Berglof, Uppsala (SE); Joachim Stadler, Freiburg (DE)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 10/473,239

(22) PCT Filed: Apr. 15, 2002

(86) PCT No.: PCT/EP02/04152

§ 371 (c)(1),
(2), (4) Date: Sep. 25, 2003

(87) PCT Pub. No.: WO02/083893

PCT Pub. Date: Oct. 24, 2002

(65) Prior Publication Data

US 2004/0126778 A1 Jul. 1, 2004

(30) Foreign Application Priority Data

Apr. 18, 2001 (SE) ............................... 0101380
Oct. 12, 2001 (SE) ............................... 0103436

(51) Int. Cl.$^7$ ................. C07H 21/00; C07G 37/00; C08G 63/68; C08G 69/14; C08G 69/26

(52) U.S. Cl. ............. 536/25.4; 536/25.41; 536/25.6; 536/54; 528/295; 528/324; 528/341; 522/56; 210/660; 210/670; 210/683

(58) Field of Search ............. 536/25.4, 25.41, 536/25.6, 54; 522/56; 528/295, 324; 210/660, 670, 683; 435/800

(56) References Cited

U.S. PATENT DOCUMENTS 5,217,593 A * 6/1993 MacConnell ............... 204/457
5,660,984 A * 8/1997 Davis et al. ............... 435/6
5,789,578 A * 8/1998 Burton et al. ............ 536/56
5,945,520 A * 8/1999 Burton et al. ............ 536/20

FOREIGN PATENT DOCUMENTS

| EP | 0 168 363 | 1/1986 |
| WO | WO95/31279 | 11/1995 |
| WO | WO97/25139 | 7/1997 |
| WO | WO01/38516 | 5/2001 |

OTHER PUBLICATIONS

Schwarz, A., et al. "Novel heterocyclic ligands for the thiophilic purification of antibodies" Journal of Chromatography B: Biomedical Applications, Elsevier Science Publishers, NL vol. 664, No. 1, Feb. 3, 1995, pp. 83–88.

Lemmens, R., et al. "S–Aryl Ligands for Chromatographic Isolation of Supercoiled Plasmid DNA" 9th Meeting of the European Society of Gene Therapy, Antalya, Turkey Nov. 2–4, 2001, pp. 18–1157–80.

* cited by examiner

Primary Examiner—Gerry Leffers
Assistant Examiner—Ramin Akhavan
(74) Attorney, Agent, or Firm—Royal N. Ronning, Jr.; Yonggang Ji; Stephen G. Ryan

(57) ABSTRACT

The present invention relates to a process for separating nucleic acid molecules, preferably open circular and supercoiled plasmid DNA and RNA molecules from each other, comprising the steps of providing a solution comprising the molecules; adsorbing the molecules to adsorbing groups on a carrier; and optionally washing the column with a suitable solution. The present process is especially suitable for large-scale isolation of supercoiled ccc DNA to be used in gene therapy.

15 Claims, 9 Drawing Sheets

ISOLATION OF DNA MOLECULES

TECHNICAL FIELD

The present invention relates to a process for separating nucleic acid molecules, such as plasmid DNA in a solution. More specifically, the present process is based on separation of oc (open circular) DNA and supercoiled ccc (covalently closed circular) DNA as well as ribonucleic acids and other deoxyribonucleic acids from each other and other components present in a solution.

BACKGROUND

The development of gene therapy and DNA vaccines has increased the demand for highly purified gene vectors such as plasmid DNA. The problem with the purification of supercoiled plasmid DNA is to completely remove other cell components such as host proteins, endotoxins, chromosomal DNA, RNA, open circular and nicked forms of plasmid DNA.

Different chromatographic methods have been used for plasmid DNA purification, such as size exclusion chromatography, or gel filtration, hydroxyapatite, ion exchange chromatography, reversed phase chromatography and hydrophobic interaction chromatography. Most of the methods lack the possibility to separate supercoiled plasmid DNA from other forms of the plasmid. Many of the available methods also use RNase to hydrolyse RNA in the cleared lysate before applying the sample to the chromatographic column. The usage of RNase is not recommendable in the preparation of plasmid DNA that is intended for human use.

Ion exchange chromatography is the most commonly used chromatography method. Plasmid DNA, chromosomal DNA and RNA all bind to anion exchangers as they have similar charge properties. Hydrophobic interaction chromatography has also been used, however, the plasmid DNA do not bind and was eluting in the flowthrough.

SUMMARY OF THE INVENTION

The object of the present invention is to provide a process for isolation of supercoiled plasmid DNA that avoids one or more of the above-discussed drawbacks. Thus, one object of the present invention is to provide a process for isolation of nucleic acid molecules on a matrix, which is efficient. The object of the invention is more specifically obtained by the process as defined in the appended claims, and by the matrix of the appended claims.

DEFINITIONS

The term "nucleic acid molecule" is understood herein to include large molecules and molecule aggregates, such as open circular plasmid DNA, supercoiled plasmid DNA and other DNA (e.g. genomic DNA) as well as RNA, such as mRNA, tRNA and sRNA.

The term "eluent" is used herein with its conventional meaning in chromatography, i.e. a solution capable of perturbing the interaction between the solid phase (adsorbent matrix) and product (nucleic acid molecule/s) and promoting selective disassociation of the product from the solid phase.

It is to be understood that any term used in the present specification, but not specifically defined herein, is to be construed in accordance with the general meaning understood by those skilled in the present technical field.

DETAILED DESCRIPTION OF THE INVENTION

In a first aspect, the present invention relates to a process for separating nucleic acid molecules from a solution, comprising the steps of (a) subjecting a mixture of nucleic acid molecules to a matrix of a carrier surface provided with an S-aryl ligand;

(b) subjecting the nucleic acid molecules to an elution step;

(c) isolating the different fractions containing the different nucleic acid molecules; and optionally washing the carrier with a suitable solution.

Thus, during step (a), the nucleic acid molecules are allowed to adsorb to the S-aryl ligands. The washing is performed after the adsorption but before the elution, as is well known in the art, in order to remove retained undesired material. Naturally, the present process can also be used in cases where nucleic acid is an undesired component of a solution, i.e. to provide a soltion purified from nucleic acid. In that case, elution of nucleic acid molecules is performed for regeneration of the column. Accordingly, a method for purification of a solution according to the invention does not necessarily include a step of elution.

In one embodiment, the process according to the invention is an isolation of nucleic acid molecules expressed in cells, and, consequently, it also comprises a first step of disintegrating the cells to provide the solution comprising nucleic acid molecules. Such disintegration is performed e.g. by lysis, such as alkaline lysis, according to standard protocols (see e.g. Maniatis, T, Fritsch, E. F. and Sambrook, J. (1982) Molecular Cloning: A Laboratory Manual, Cold Spring Harbour Laboratory Press, Cold Spring Harbour, N.Y.).

In another embodiment, the present process comprises the further step of eluting the supercoiled plasmid DNA molecules by contacting a suitable eluent with said matrix. Thus, the elution step can be performed as a dynamic or batch procedure. Elution is conveniently performed according to well-known principles, such as by a gradient of decreasing conductivity as is also illustrated in the experimental part below.

Thus, the process according to the invention is utilised e.g. for purification of nucleic acids for use in gene therapy, DNA vaccines and laboratory studies related to gene therapy. In an advantageous embodiment, the present process will provide isolated supercoiled plasmid DNA of acceptable gene therapy grade. More specifically, it is predicted that in a near future, there will be an increasing demand of plasmid DNA, in large quantities for use in gene therapy as carriers or vectors of genetic material. As mentioned above, the previously described methods for isolation of such carriers have not been satisfactory to this end, and the process according to the present invention is thus the first to enable large scale processing of nucleic acid molecules for medical and diagnostic use, in particular separating oc plasmid DNA and ccc plasmid DNA. An additional advantage with the present method is that it is conveniently adapted to automation. For example, automation on ÄKTA™explorer (Amersham Pharmacia Biotech AB, Uppsala, Sweden) has been shown to result in high amounts of homogeneous plasmid DNA, more specifically in more than 98% supercoiled plasmid DNA.

Plasmids isolated in accordance with the invention can be of any origin. Most commonly, microorganisms like bacteria, such as *E. coli*, are used for culturing the plasmids, but the use of host cells is not limited and can be prokaryotic or eukaryotic cells. The host cells harbouring the plasmid can be cultivated in a number of ways well known in the art, e.g. in incubator, bioreactor, fermentor etc. The plasmid isolated according to the invention can be of virtually any size, e.g. in the range of about 1 kb up to about 20 kb. As an upper limit, the isolation of cosmids and artificial chromosomes is also encompassed, the size of which may be up to about 50 kb and 500 kb, respectively.

Plasmids can be of a high copy number or low copy number and can carry any gene, either genomic or synthetic, encoding protein or peptide of interest, from any source. The culturing of the host cells, as well as the exploitation of the plasmid for gene therapy, is well known in the state of the art.

After culturing the host cells containing the plasmid, the cells are recovered by e.g. centrifugation or filtration. The cells can be stored, for example in a freezer, or processed immediately.

As mentioned above, when the plasmid DNA according to the invention has been produced in a cell, lysis thereof is advantageously performed by alkaline lysis. The lysate may then be treated with metal ions, such as of divalent alkaline earth metal ions, to precipitate impurities and specifically RNA and chromosomal DNA. When the precipitated material has been removed, the solution can be applied to the column. (For a detailed disclosure of metal ion precipitation methods in this context, see e.g. WO9916869 in the name of Amersham Pharmacia Biotech.)

In an advantageous embodiment, the matrix material used is present as column chromatography material, and the carrier material onto which the ligand is bound, is any suitable inorganic or organic material. Inorganic materials are glass, silica, or other inert particulate minerals. Such matrices can be any matrix available in the market. There are many commercial products available based on different resins or polymer, e.g. agarose or cross-linked agarose (such as SEPHAROSE™ Media, Amersham Pharmacia Biotech), dextran (such as SEPHADEX™ Media, Amersham Pharmacia Biotech), polystyrene/divinylbenzene (MONOBEADS™ Media, SOURCE™ Media, Amersham Pharmacia Biotech), coated polystyrene, acrylic polymer, dextran acrylic polymer (SEPHACRYL™ Media, Amersham Pharmacia Biotech), vinylic grafted polymer, or vinylic polymer, different silica based resins such as silica-dextran, silica-acrylic polymer and silica-polyethyleneimine.

The present process may be performed with the matrix as an expanded bed, as a packed bed or in a batch mode. In packed bed adsorption, the adsorbent is packed in a chromatographic column and all solutions used during a purification process flow through the column in the same direction. In expanded bed adsorption however, the adsorbent is expanded and equilibrated by applying a liquid flow through the column. A stable fluidized expanded bed is formed when there is a balance between particle sedimentation or rising velocity and the flow velocity during application of the sample and washing steps. In the elution step, the adsorbent is precipitated and behaves like a packed bed adsorbent.

The ligand attached to the carrier material to form the matrix of the invention can be a mercapto-pyridine, mercaptoalkylpyridine, where the mercapto- and mercaptoalkyl groups are attached in ortho, and meta position respectively, in relation to the pyridyl-nitrogen. Hereby it is the mercapto-group that is attached to the carrier material via a thioether binding. Further, aryl groups forming part of the ligand are phenyl, benzyl, toluyl, phenethyl, naphtyl, imidazolyl, pyrazolyl, pyrazinyl, pyrimidinyl, pyridazinyl, piperidinyl, morpholinyl, piperazinyl, indolyl, quinolinyl, purinyl. Further substituents can also be added on the aromatic ring. By providing the present S-aryl ligands with additional substituents, a large range of different separation media can be designed in order to obtain desired binding and elution characteristics. For example, it may be desired to shift the elution profile in order to allow use of a less concentrated eluent for the desorption step. The substituents can for example be one or more amine groups, nitro groups, ether groups, thiol groups and/or halogens, such as fluorine. These additional substituents can also comprise further carbon atoms, as desired. Also, as the skilled in this field will realise, carbon atoms can be exchanged for heteroatoms in the above discussed ring structures. It is to be understood herein that the term "S-aryl ligand" comprises a large range of compounds that can be substituted to a desired extent, some of which will be exemplified below in FIG. 1. The ligand density is 10–500 μmole/mL carrier, preferably in the range 10–100 μmole/mL carrier.

The eluent used in the present invention is pH neutral (preferably a pH of 6.5 to 8.5) eluent, preferably an ammonium sulphate solution having a concentration of 0.5 to 4 M, preferably 1.5 to 2.0 M at which oc DNA is not bound in contrast to the ccc form. After loading of the complete sample to the column, bound ccc plasmid DNA can subsequently be eluted from the column by using decreasing ammonium sulphate concentrations. RNA molecules can be eluted from the column by using even lower concentrations of ammonium sulphate.

In a second aspect, the invention relates to matrices containing a mercapto-aryl moiety, which matrices selectively separates nucleic acid plasmid molecules, such as oc DNA, ccc DNA, and RNA molecules. Hereby, the mercapto-group may be substituted directly onto the aryl group, or via an alkylene chain having 1 to 7 carbon atoms. In laboratory tests made it was shown that neither 4-(2-mercaptoethyl) pyridine, or 2-(2-oxoethyl)pyridine had the ability of separating ocDNA and cccDNA.

In one embodiment, the matrix particles are of a mean size in the range of about 10–300 μm, e.g. within a range of 10–20, 20–50, 50–100, 100–200 or 200–300 μm. However, the particles can advantageously be prepared in any size for which commercially available sieve equipment is exist, such as 250, 212, 180, 150, 125, 106, 90, 75, 63, 45, 37, 30, 25, 20, 15 μm.

In one embodiment, which is especially advantageous for the separation of nanoparticles, such as plasmids or virus, the present method will use a matrix comprised of one or more of the above discussed S-aryl compounds as ligands coupled to superporous particles. The average superpore diameter of the superporous matrix particles used in the present embodiment will be at least about 4 μm, such as about 5–10 or about 10–20 μm, and maybe of a value of up to about 25 μm, such as about 20–30 or even about 30–40 μm. However, in the present context, it is to be understood that the term "superporous" relates to particles wherein the pores are large enough so as to be an essential part of the structure of the particles, i.e. to penetrate the particles to a much deeper extent than conventional particles having a porous surface layer but a central portion which is essentially solid. In one especially advantageous embodiment, the adsorption step is run under dynamic conditions. Accordingly, the superporous particles used in this embodiment are to a substantial portion penetrated with pores, while they are still designed to be sufficiently rigid to keep their original appearance, i.e. not to collapse, during a dynamic flow procedure.

DETAILED DESCRIPTION OF THE DRAWINGS

Figure 1:
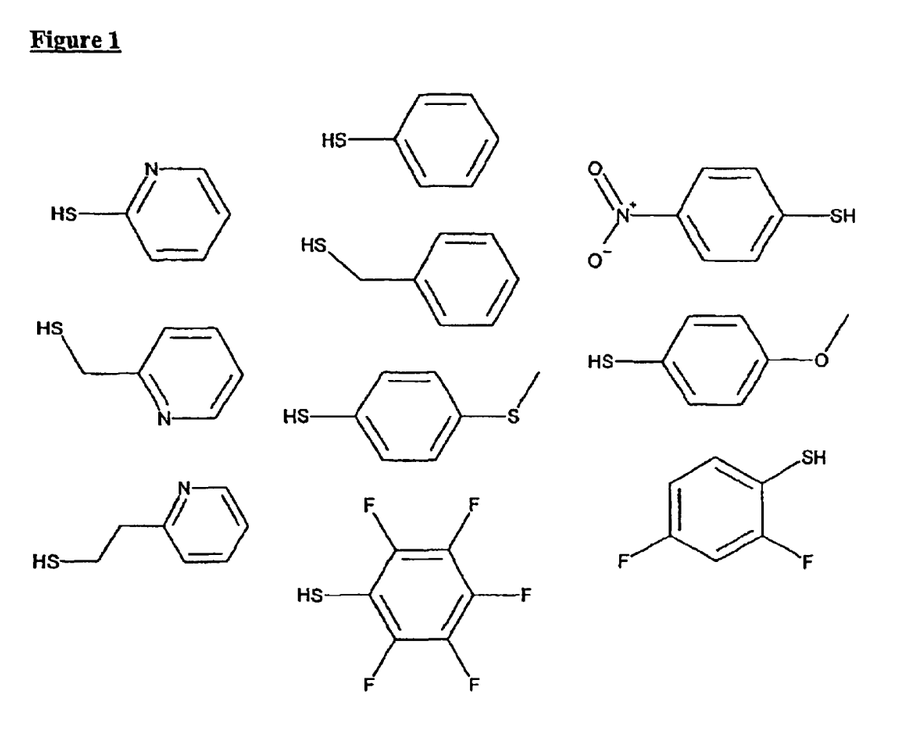
FIG. 1 shows examples of S-aryl compounds reacted with SEPHAROSE 6 FAST FLOW™ Media, which compounds do possess separation properties.

FIG. 1 shows examples of a variety of S-aryl compounds reacted on a SEPHAROSE 6 FAST FLOW™ Media Column. As appears from this drawing, the S-aryl compounds can be provided with different substituents, each of which can result in binding and elution properties that may prove advantageous for different purposes.

Figure 2:
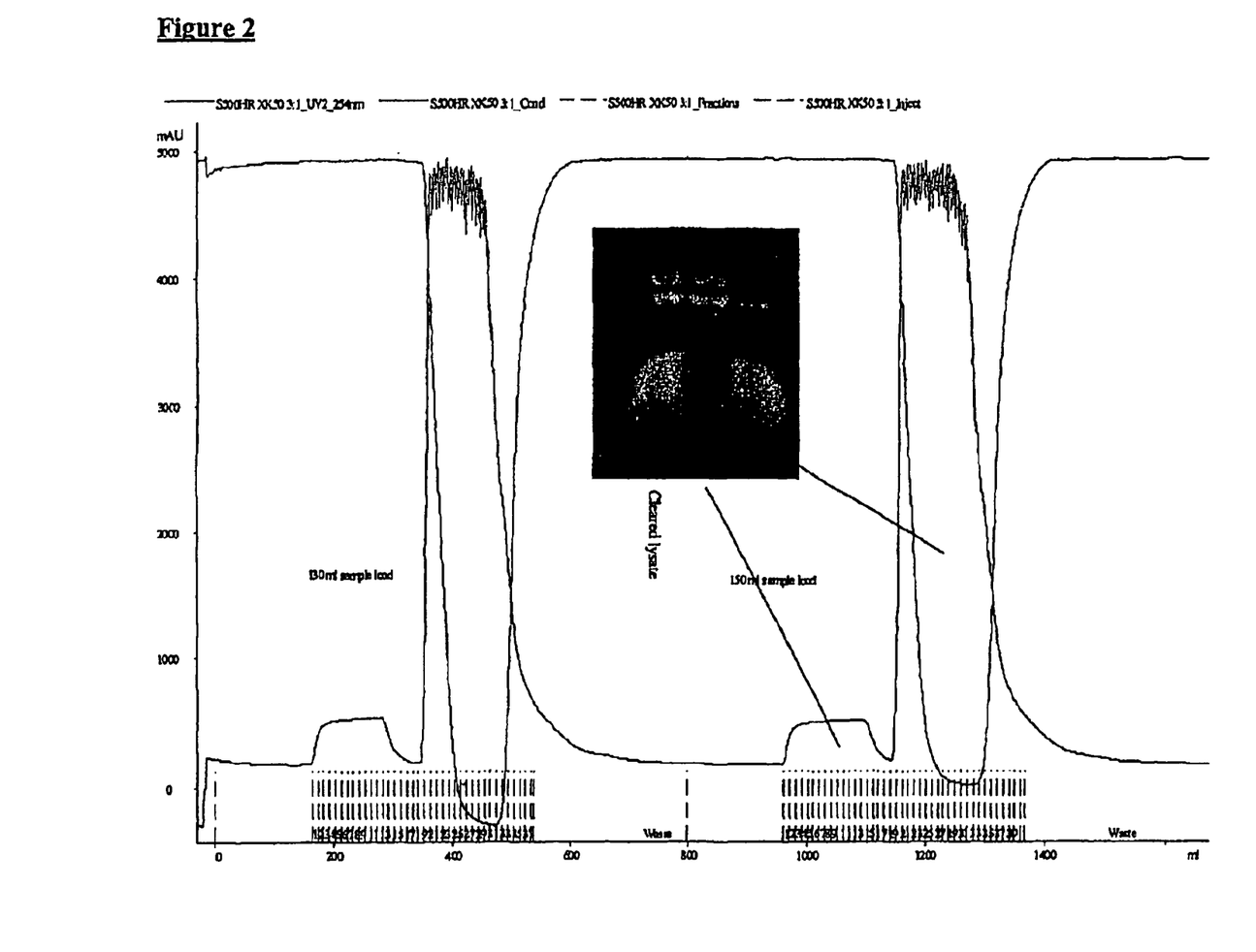
FIG. 2 shows the two chromatograms obtained after loading respectively 130 and 150 ml of cleared lysate on a SEPHACRYL™ S-500 HR Media, run in 2M ammonium sulphate. The insert shows the agarose gel electrophoresis analysis of selected fractions as well as an aliquot of the starting material.

FIG. 2 shows the results obtained after a group separation of plasmid DNA versus RNA of cleared lysate on SEPHACRYL™ S-500 HR Media in a XK 50/30 column with a bed height of 20 cm. The column is equilibrated in 2 M $(NH_4)_2SO_4$ in 25 mM Tris, pH 7.9 with a conductivity of 216 mS/cm and 130 respectively 150 ml cleared lysate is loaded at a flow rate of 30 cm/hr. Once the sample is applied to the column, the flow rate is increased to 60 cm/hr, and the void volume is collected. After total elution of all sample and re-equilibration of the column, the next sample is loaded. Analysis of selected fractions on a 1% agarose gel electrophoresis shows the presence of open circular and supercoiled plasmid DNA together with RNA in the cleared lysate preparation. In the excluded volume of the gel filtration, no presence of RNA can be detected. However, most of both open circular and supercoiled plasmid DNA can be found in these fractions. The excluded volume is collected and used in subsequent chromatography steps.

Figure 3A:
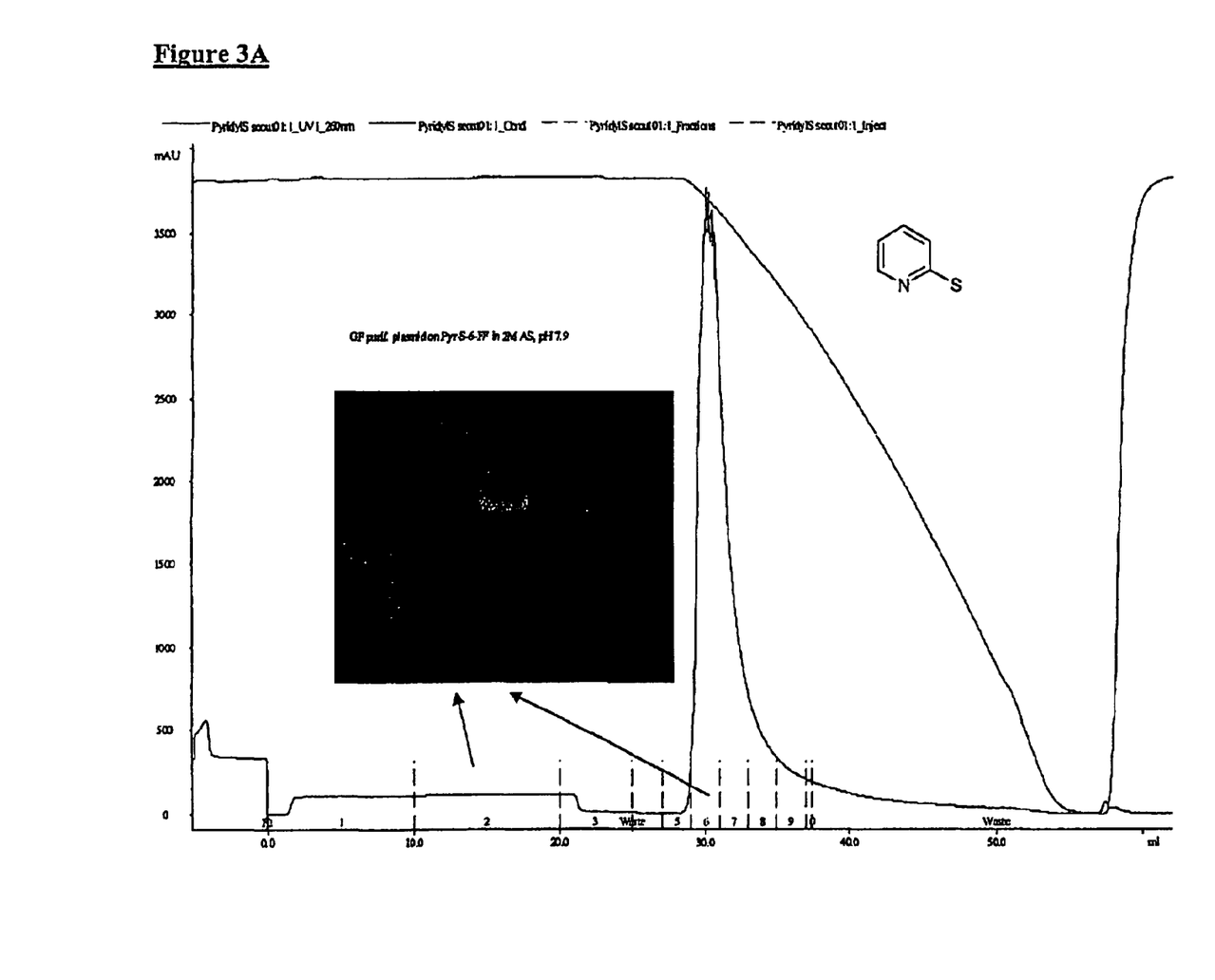
FIGS. 3A, B and C illustrate the results obtained after chromatography on SEPHAROSE 6 FAST FLOW™ Media Column with a number of different S-aryl ligands, as indicated on the chromatograms. Inserts show agarose gel electrophoresis analysis of selected fractions.

FIG. 3A depicts the chromatogram acquired after loading the plasmid DNA sample on a Pyridyl-S SEPHAROSE 6 FAST FLOW™ Media Column and eluting with $H_2O$-gradient. The pyridyl-S ligand is depicted in the upper-right corner. Pyridyl-S SEPHAROSE™ 6FF Media Column is equilibrated with 2 M $(NH_4)_2SO_4$ in 25 mM Tris, pH 7.9 (216 mS/cm) in a 4.6/15 PEEK™ Column after which 20 ml of sample obtained after gel filtration chromatography is loaded on the Pyridyl-S SEPHAROSE™ 6FF Media Column at a flow rate of 45 cm/hr. After washing off all unbound material with equilibration buffer, the supercoiled plasmid DNA is eluted by decreasing the conductivity by applying a gradient over 2 column volumes with $H_2O$. One peak elutes when the conductivity reaches 212 mS/cm. Once the total gradient has been established, the column is re-equilibrated with 2 M $(NH_4)_2SO_4$ in 25 mM Tris, pH 7.9 (216 mS/cm).

Selected fractions from void volume and elution peak are analyzed for the presence of the different forms of plasmid DNA on a 1% agarose gel electrophoresis. The insert shows that under these conditions, most of the open circular plasmid DNA does not bind to the Pyridyl-S SEPHAROSE 6 FAST FLOW™ Media, while the supercoiled DNA binds to the media and can be eluted by lowering the conductivity to less than 212 mS/cm. The last lane on the agarose gel represents a five times dilution of the elution peak containing the supercoiled plasmid DNA.

Figure 3B:
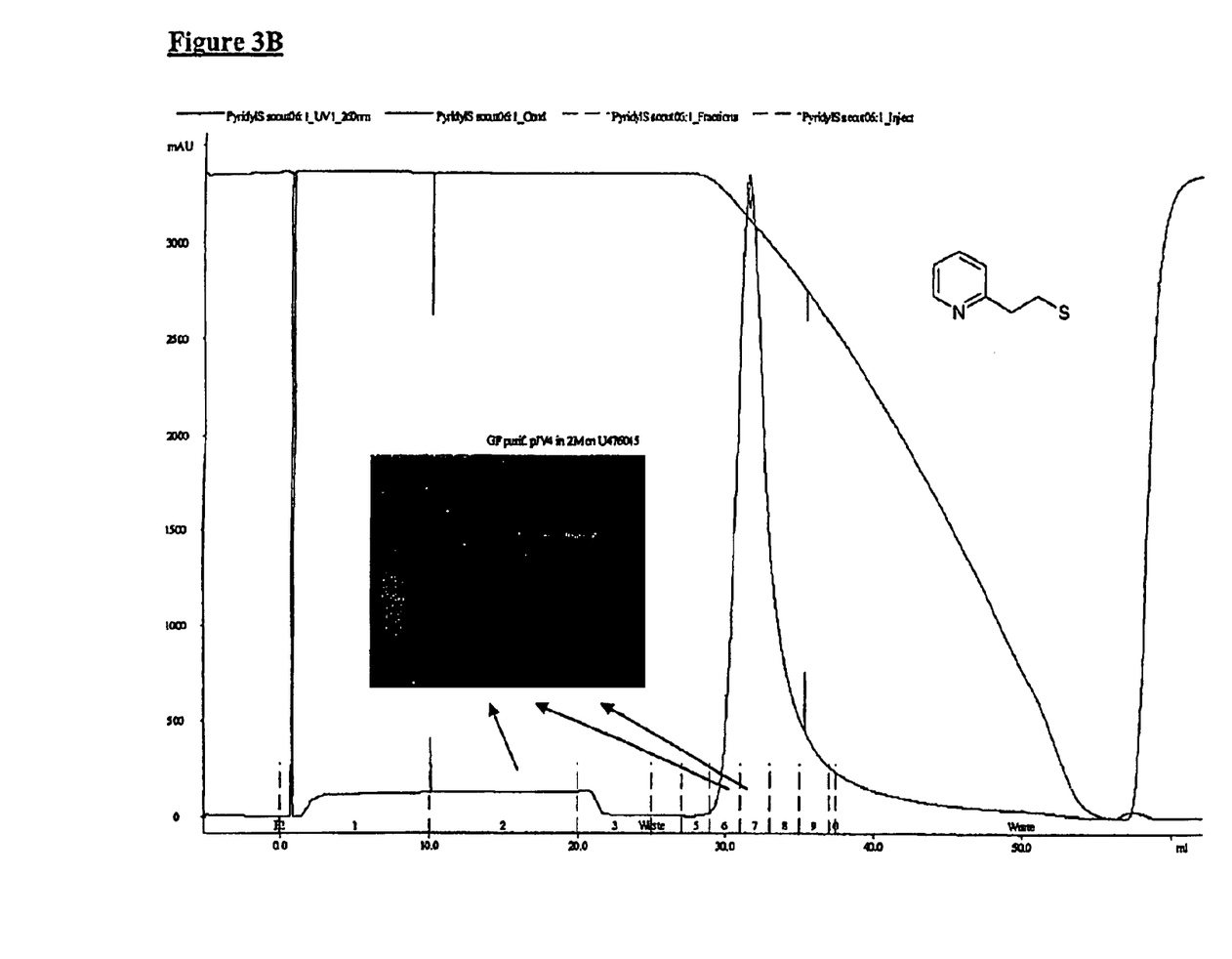

FIG. 3B represents the results obtained after loading the plasmid DNA sample obtained after gel filtration on the SEPHACRYL™ S-500 HR Media Column on a 2-mercaptoethylpyridine SEPHAROSE 6 FAST FLOW™ Media Column. The ligand used in this experiment is depicted in the upper-right corner of the chromatogram. After equilibration of the column with 20 ml of the sample obtained in the experiment illustrated in FIG. 1 is loaded on the column at 45 cm/hr. After 2 column volumes of washing buffer, the supercoiled plasmid DNA is eluted from the column by decreasing the conductivity with a gradient of $H_2O$. Once the conductivity reaches a value of 209 mS/cm, the bound material elutes from the column. As illustrated in the 1% agarose gel electrophoresis, this elution peak contains mainly supercoiled plasmid DNA while the open circular plasmid DNA can be found in the void volume, and thus does not bind to the media under these settings.

Figure 3C:
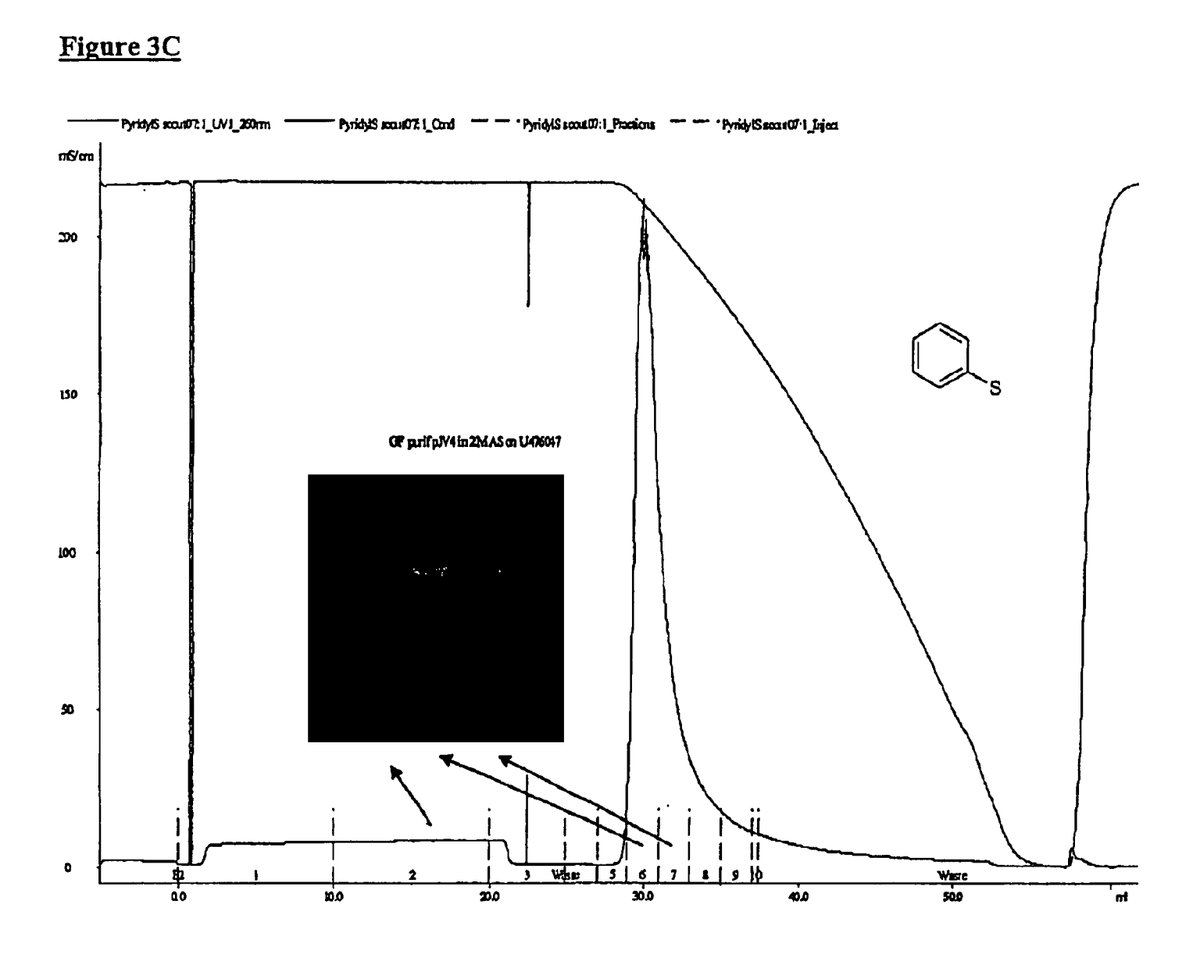

FIG. 3C shows the chromatogram obtained with the ligand depicted in the upper-right corner of the figure. The phenyl-S SEPHAROSE 6 FAST FLOW™ Media Column is equilibrated with 2 M $(NH_4)_2SO_4$ in 25 mM Tris, pH 7.9 (216 mS/cm) before loading 20 ml of the void volume of the gel filtration on the media at a flow rate of 45 cm/hr. Unbound material is washed off with 2 M $(NH_4)_2SO_4$ in 25 mM Tris, pH 7.9 (216 mS/cm), and bound material is eluted by lowering the conductivity with a $H_2O$-gradient. At a conductivity of 214 mS/cm, the material starts to elute from the media. Analysis on a 1% agarose gel electrophoresis shows the presence of only open circular plasmid DNA in the flow through. Supercoiled plasmid DNA binds to the column and is detected in the elution peak.

Figure 4:
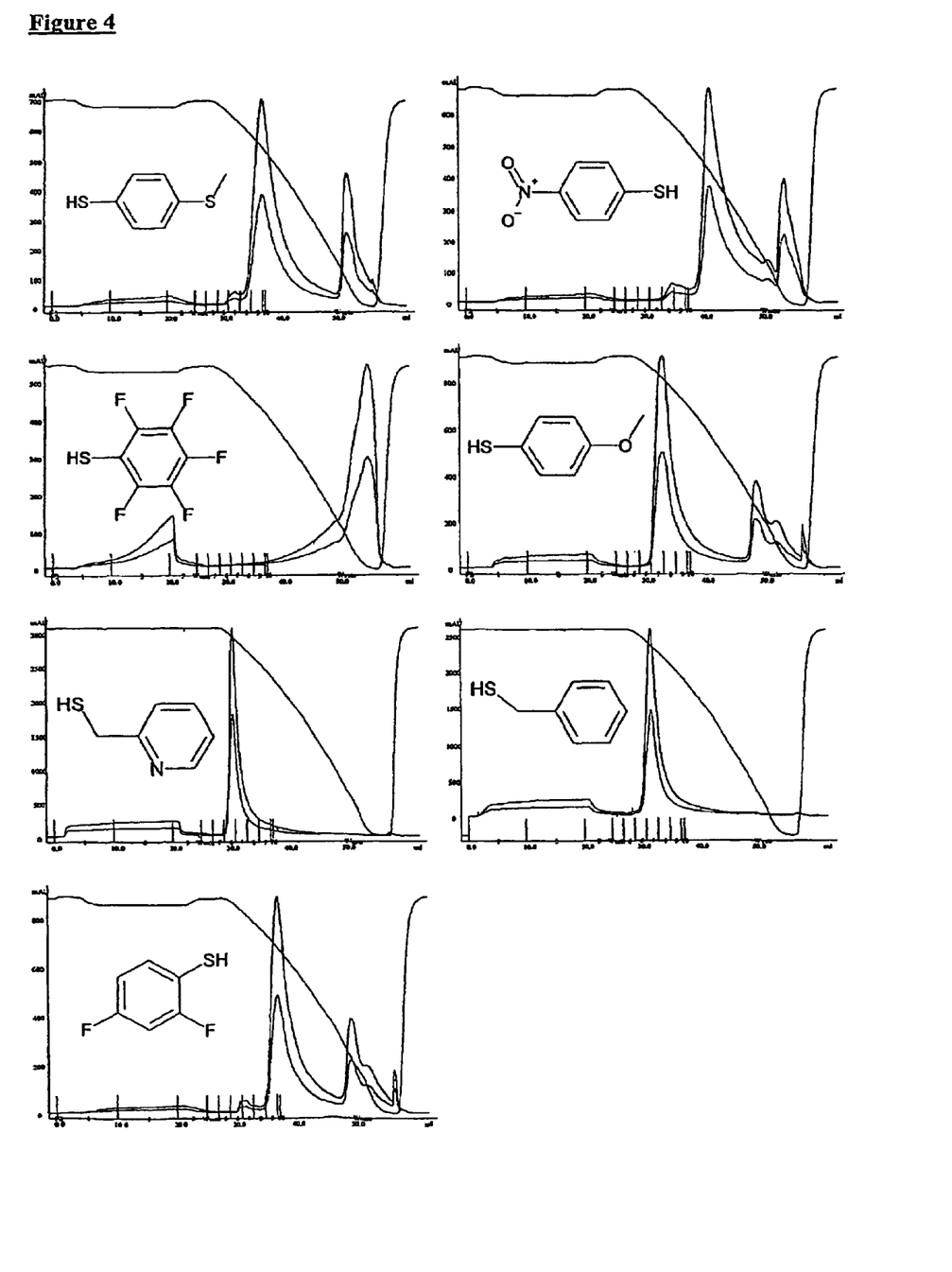
FIG. 4 illustrates results obtained after chromatography on SEPHAROSE 6 FAST FLOW™ Media with a number of different S-aryl ligands, as indicated on the chromatograms.

FIG. 4 shows a number of chromatograms obtained with some of the different ligands depicted in FIG. 1. For every chromatogram, the ligand is presented in the upper-right corner of the figure. The S-aryl SEPHAROSE 6 FAST FLOW™ Media Column is equilibrated with 2 M $(NH_4)_2SO_4$ in 25 mM Tris, pH 7.9 (220 mS/cm) before loading 20 ml of the void volume of the gel filtration on the media at a flow rate of 45 cm/hr. Bound material is eluted by decreasing the conductivity with a gradient to pure $H_2O$. By comparing the different chromatograms, it becomes clear that by changing the ligand properties, the binding and elution conditions for plasmid DNA can be modified.

Figure 5:
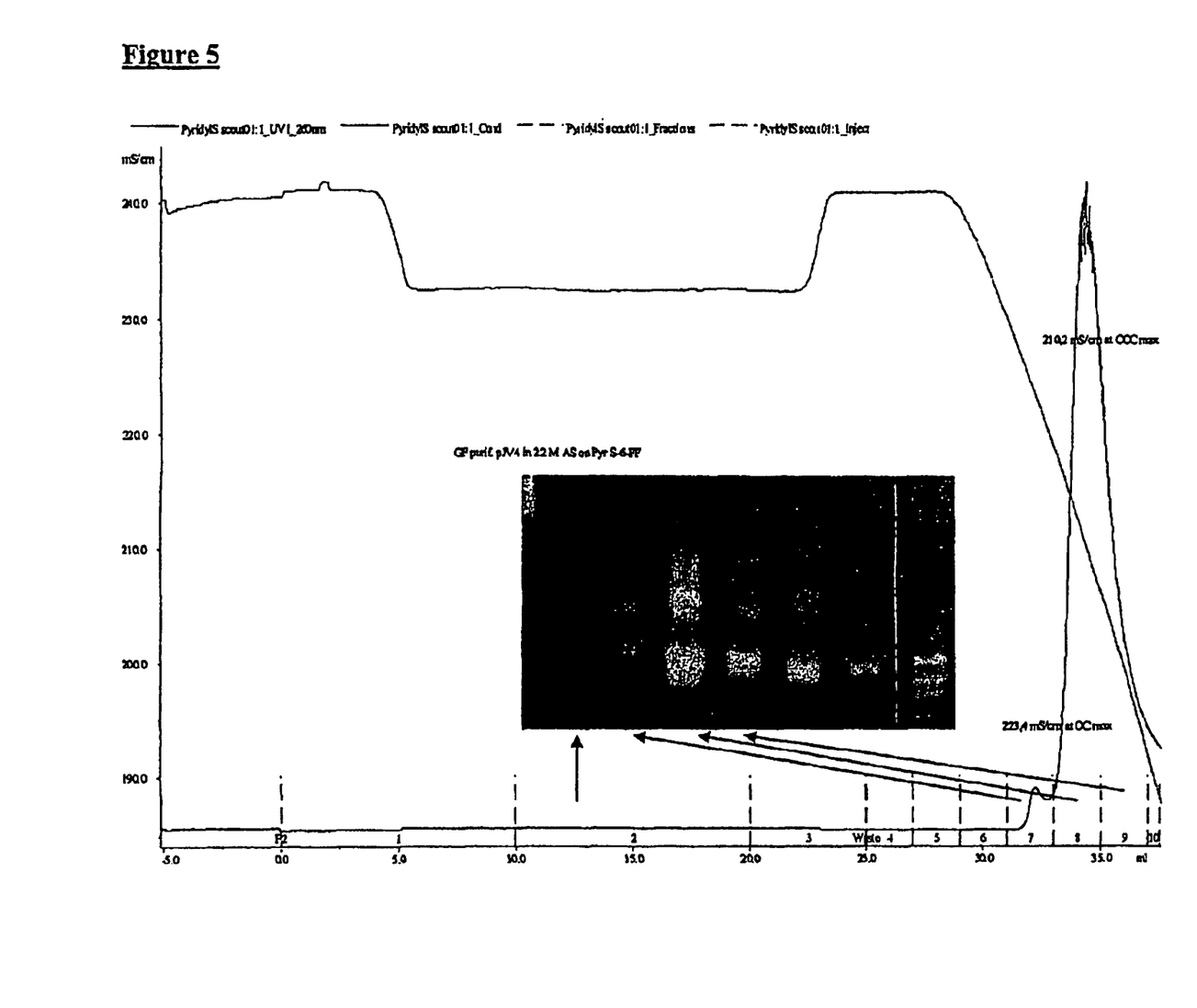
FIG. 5 presents the chromatogram gained after loading the sample (prepurified by gel filtration) on Pyridyl-S SEPHAROSE 6 FAST FLOW™ Media under high conductivity conditions (>240 mS/cm).

FIG. 5 illustrates the results obtained after loading the plasmid DNA sample on Pyridyl-S SEPHAROSE 6 FAST FLOW™ Media Column under high conductivity conditions. The Pyridyl-S SEPHAROSE 6 FAST FLOW™ Media Column is equilibrated with 2.4 M $(NH_4)_2SO_4$ in 25 mM Tris, pH 7.9 (240 mS/cm). The sample obtained after gel filtration on the SEPHACRYL™ S 500 HR Media Column is adjusted to 240 mS/cm before loading 20 ml on the Pyridyl-S SEPHAROSE™ 6FF Media Column at 45 cm/hr. Unbound material is washed out using the same buffer, and elution is started by decreasing the conductivity with a $H_2O$-gradient. Two elution peaks are detected under these conditions, and selected samples are analyzed on a 1% agarose gel electrophoresis. Under these circumstances, both open circular and supercoiled plasmid DNA are found to bind the Pyridyl-S SEPHAROSE™ 6 FF Media Column, but both tend to elute at different conductivity-values and thus factions enriched in either open circular or supercoiled DNA can be acquired.

Figure 6:
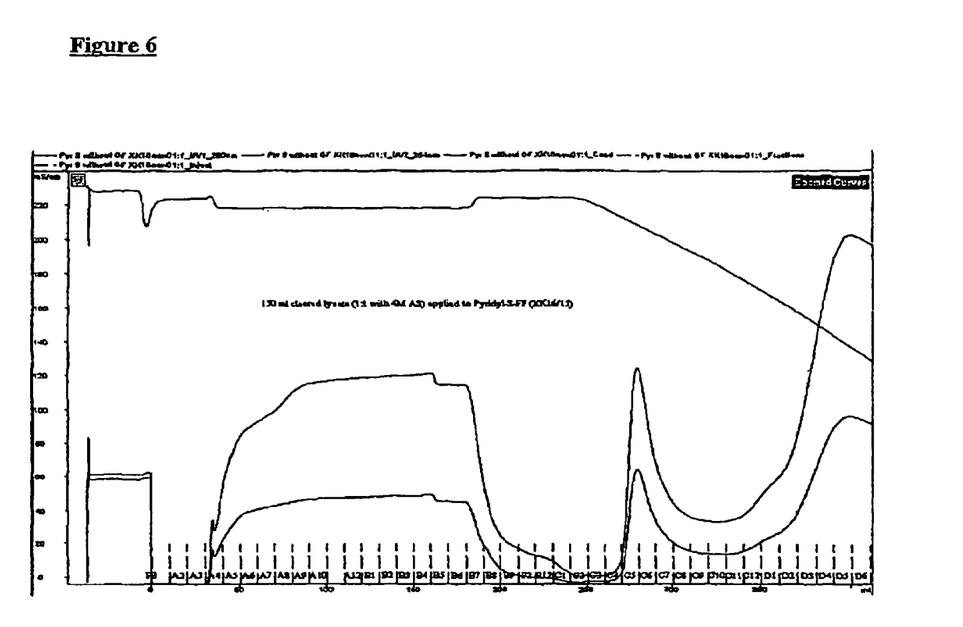
FIG. 6 shows the results obtained after performing chromatography of cleared lysate on Pyridyl-S SEPHAROSE 6 FAST FLOW™ Media in a XK16/15 column.

FIG. 6 shows the results obtained after performing chromatography of cleared lysate on Pyridyl-S SEPHAROSE 6 FAST FLOW™ Media in a XK16/15 column. The Pyridyl-S SEPHAROSE 6 FAST FLOW™ Media Column is equilibrated with 2 M $(NH_4)_2SO_4$ in 25 mM Tris, pH 7.5 (224 mS/cm) after which 150 ml of cleared lysate is loaded at a flow rate of 90 cm/hr. Unbound material is washed out, and the bound material is eluted by decreasing the conductivity by applying a gradient with water over the column. Open circular plasmid DNA does not bind to the matrix, while both supercoiled plasmid DNA and RNA do bind with the Pyridyl-S SEPHAROSE™ 6 FF Media Column. Both can however be eluted at different conductivities, where supercoiled plasmid DNA starts eluting from the column at 211 mS/cm, while RNA only elutes in a broad peak once the conductivity is below 170 mS/cm.

Figure 7:
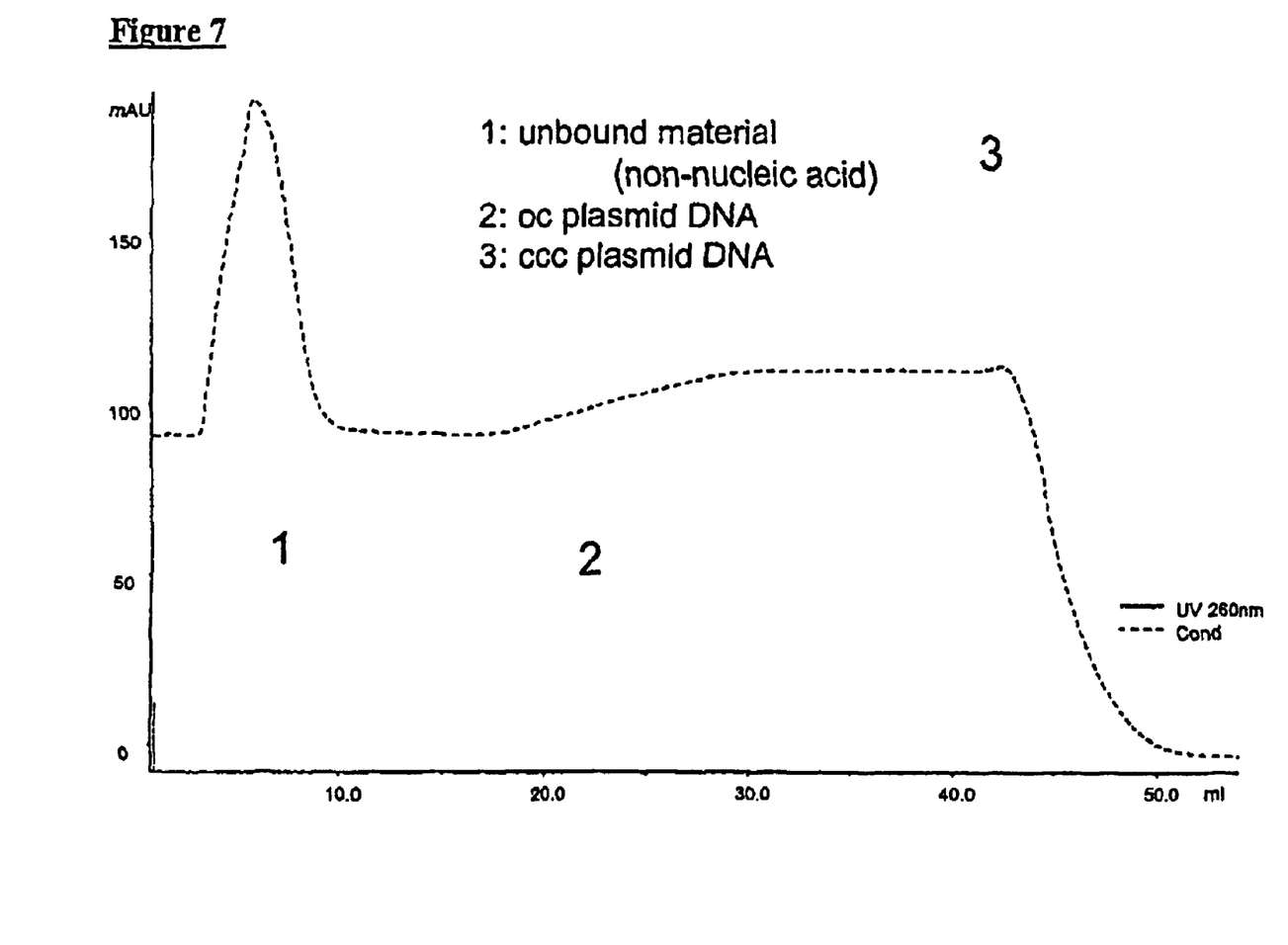
FIG. 7 is a chromatogram using demonstrating the use of $Na_2SO_4$ during adsorption of plasmid DNA to an S-aryl ligand according to the invention.

FIG. 7 illustrates how plasmid DNA is loaded on a column according to the invention preconditioned in 3.0 M $Na_2SO_4$, 10 mM EDTA, 100 mM Tris-HCl, pH 7.0 and eluted with a gradient to 1 M NaCl.

EXPERIMENTAL PART

Below, the present invention will be described by way of examples provided only as an illustration and not to be construed as limiting the scope of the invention as defined by the appended claims in any way. All references included below or else-where in the present application are hereby included herein by reference.

Preparation of Ligand Comprising Agarose Beads

SEPHAROSE 6 FAST FLOW™ Media Column (Amersham Pharmacia Biotech) was activated with epoxy groups according to Hermanson et al [Immobilized Affinity Ligand Techniques, Academic Press (1992), p. 118]. The ligand density was approximately 50 µmol epoxy/mL carrier. The S-aryl reagents (See FIG. 1), 50 µmol/mL carrier, were reacted with the epoxyactivated SEPHAROSE™ Media at pH 10.5. The reactions were performed at 45° C. under nitrogen atmosphere over night. After the reaction, the gel was cooled and washed with acetone and finally water. The ligand concentration obtained were in the range of 30–50 µmol/mL carrier.

Cell Culture

An inoculum of *E. Coli* TG1 cells containing a pUC19 plasmid with JV4-insert are grown in 2YT medium to a OD of 4, after which 40 ml is transferred to a 10 liter culture in a Biostat ED reactor. At an OD of 13.6, the cells are harvested, centrifuged for 40 minutes at 4200 rpm in a Sorvall RC12BP rotor and the cell pellet is stored at −70° C.

Alkaline Lysis 25 g of bacteria are resuspended in 50 ml of ice-cold S buffer (61 mM glucose, 10 mM Tris, 50 mM EDTA pH 8.0). Another 130 ml of buffer S is added. Under constant gentle stirring, 390 ml of buffer P2 (0.2 M NaOH, 1% SDS) is added. After 10 minutes of gentle stirring at room temperature to assure complete mixing, 293 ml ice-cold buffer P3 (3M potassium acetate, pH 5.5) is added. Under gentle stirring for 20 minutes, the solution is incubated on ice before storing overnight at 4° C. The next day, the mixture is centrifuged for 30 minutes at 10.000 rpm at 4° C. in a GSA rotor and the supernatant is filtered through filter paper to obtain cleared lysate.

Sample Preparation

Cleared lysate has been processed as follows:
a) adjusted to 2M ammonium sulphate by addition of equal amounts (volumes) of 4M ammonium sulphate, or preferentially
b) sample prepurification by size exclusion (group separation and buffer exchange) on SEPHACRYL™ S-500 HR Media (Amersham Pharmacia Biotech), pre-equilibrated and run in 2M ammonium sulphate. A SEPHACRYL™ S-500 HR Media (XK 50/30 column, 20 cm bed height) is equilibrated with 2 M $(NH_4)_2SO_4$ in 25 mM Tris, pH 7.9. Up to 0.4 CV of cleared lysate is loaded on the column at 30 cm/hr. Once all sample is loaded on the column, the elution speed is adjusted to 60 cm/hr, and the flow through containing plasmid DNA is collected for further experiments (see FIG. 2).

Chromatography

Several S-aryl SEPHAROSE 6 FAST FLOW™ Media are packed in 4.6/15 PEEK™- or XK 16/15 glass-columns (15 cm bed height) at 140 cm/hr and all columns are equilibrated in 2 M (NH4)2SO4 in 25 mM Tris, pH 7.9 resulting in a conductivity of more then 215 mS/cm (corrected for 25□C temperature) at 45 cm/hr. 20–150 ml of cleared lysate preparations (according to a) or b), see above) is then loaded to the column at the same flow rate. After a wash of 2 column volumes, the bound material is eluted from the media with a gradient to H2O over 10 column volumes. During the run, absorption at 260 nm is recorded. Different fractions are collected and a number of them are analysed on a 1% agarose gel electrophoresis stained by ethidium bromide and visualised by UV (see FIGS. 3 A–C, FIG. 4, FIG. 5 and FIG. 6).

What is claimed is:

1. A process for separating nucleic acid molecules form a solution, comprising the steps of:
   (a) subjecting a mixture of nucleic acid molecules to a matrix of a carrier surface with an S-aryl ligand containing a pyridyl moiety attached thereto, such that the nucleic acids are adsorbed onto said S-aryl ligand containing a pyridyl moiety;
   (b) subjecting the nucleic acid molecules to an elution step;
   (c) isolating one or more different fractions containing the different nucleic acid molecules; and
   (d) optionally washing the carrier with a washing solution wherein the nucleic acid molecules include open circle plasmid DNA, closed circle complex plasmid DNA, genomic DNA and RNA.

2. The process of claim 1, further comprising an initial step of lysing cells which express the nucleic acid molecules to provide the solution comprising nucleic acid molecules.

3. The process of claim 1, which further comprises a step of eluting the nucleic acid molecules by contacting with an eluent.

4. The process of claim 1, wherein the carrier is an inorganic matrix.

5. The process of claim 4, wherein the carrier is glass.

6. The process of claim 4, wherein the carrier is a zeolite.

7. The process of claim 4, wherein the carrier is a silica.

8. The process of claim 1, wherein the carrier is an organic matrix.

9. The process of claim 8, wherein the carrier is a resin or polymer.

10. The process of claim 9, wherein the carrier is selected from the group consisting of agarose, cross-linked agarose, dextran, polystyrene/divinylbenzene, coated polystyrene, acrylic polymer, dextran acrylic polymer, vinylic grafted polymer and vinylic polymer.

11. The process of claim 9, wherein the carrier includes one or more silica based resins in the form of silica-dextran, silica-acrylic polymer or silica-polyethyleneimine.

12. The process of claim 1, wherein the carrier is present as a membrane which comes in contact with the nucleic acid molecule mixture.

13. The process of claim 1, wherein the carrier is present as a chromatography matrix in a column through which the nucleic acid molecule mixture is passed.

14. The process of claim 1, wherein the S-aryl ligand is a pyridyl-S ligand having the S-moiety bound in 2 (ortho) or 3 (meta) position to the pyridyl nitrogen atom.

15. The process of claim 14, wherein the S-aryl ligand is separated from the pyridyl moiety via an alkylene chain having 1 to 7 carbon atoms.

* * * * *